United States Patent [19]

Layman et al.

[11] Patent Number: 4,514,294

[45] Date of Patent: Apr. 30, 1985

[54] APPARATUS FOR DECONTAMINATING HYDROCARBONS CONTAINING PCB

[75] Inventors: Robert G. Layman, Box 417 R, Barto, Pa. 19504; Linwood B. Kemp, 5 Rega La., Birdsboro, Pa. 19508

[73] Assignees: Robert G. Layman; Linwood B. Kemp, both of Birdsboro, Pa.

[21] Appl. No.: 538,307

[22] Filed: Oct. 3, 1983

[51] Int. Cl.³ ............................................. B01D 57/00
[52] U.S. Cl. ...................................... 210/87; 210/181; 210/195.1; 210/202; 210/241; 210/909
[58] Field of Search .................. 210/87, 88, 181, 182, 210/195.1, 202, 205, 206, 241, 258, 259, 295, 439, DIG. 5, 909

[56] References Cited

U.S. PATENT DOCUMENTS

| 3,388,800 | 6/1968 | MacGregor | 210/439 |
| 3,491,882 | 1/1970 | Elam | 210/799 |
| 3,630,365 | 12/1971 | Woodbridge et al. | 210/241 |
| 4,377,471 | 3/1983 | Brown et al. | 208/262 |
| 4,379,746 | 4/1983 | Norman et al. | 208/262 |
| 4,379,752 | 4/1983 | Norman | 210/712 |
| 4,383,920 | 5/1983 | Muller et al. | 210/264 |

Primary Examiner—Ivars Cintins
Attorney, Agent, or Firm—Seidel, Gonda & Goldhammer

[57] ABSTRACT

A mobile vehicle is utilized to process hydrocarbons having high toxicity due to the presence of PCB. Hydrocarbons containing PCB are blended with metallic sodium at a temperature of about 130° C. and thereafter the mixture is separated into its components one of which is a hydrocarbon containing less than about 2 ppm of PCB.

6 Claims, 3 Drawing Figures

APPARATUS FOR DECONTAMINATING HYDROCARBONS CONTAINING PCB

BACKGROUND OF THE INVENTION

The toxicity problem associated with hydrocarbons containing PCB is old and well-known. A number of solutions has been suggested heretofore. For example, see U.S. Pat. Nos. 4,377,471, 4,379,746 and 4,379,752.

While a number of different processes have been suggested heretofore, they do not take into consideration an important aspect of the problem. Thus, the contaminated hydrocarbons exist in a large number of locations in different parts of the country. It is impractical to build a plant for processing the contaminated hydrocarbons at each such location. It is also impractical to ship the hydrocarbons to a processing plant.

The present invention solves all of the presently known problems associated with hydrocarbons contaminated with PCB.

SUMMARY OF THE INVENTION

The present invention is directed to an apparatus for removing PCB from hydrocarbons. The method of the present invention is preferably practiced by way of a mobile vehicle adapted to process the hydrocarbons. On the vehicle there is provided apparatus for heating the hydrocarbons which are substantially free of water to a temperature of about 130° C. Then metallic sodium, preferably finely divided, is melted and added to the hydrocarbons in an amount sufficient to reduce PCB to less than 2 ppm. Thereafter, the mixture is separated so as to remove the reactant sodium chloride and phenyl polymer from the hydrocarbons. Thereafter, the hydrocarbon is filtered and then stored.

It is an object of the present invention to provide novel apparatus for removing PCB from hydrocarbons in a manner which is simple, reliable, effective, and inexpensive.

Other objects and advantages will appear hereinafter.

For the purpose of illustrating the invention, there is shown in the drawings a form which is presently preferred; it being understood, however, that this invention is not limited to the precise arrangements and instrumentalities shown.

DETAILED DESCRIPTION

Figure 1:
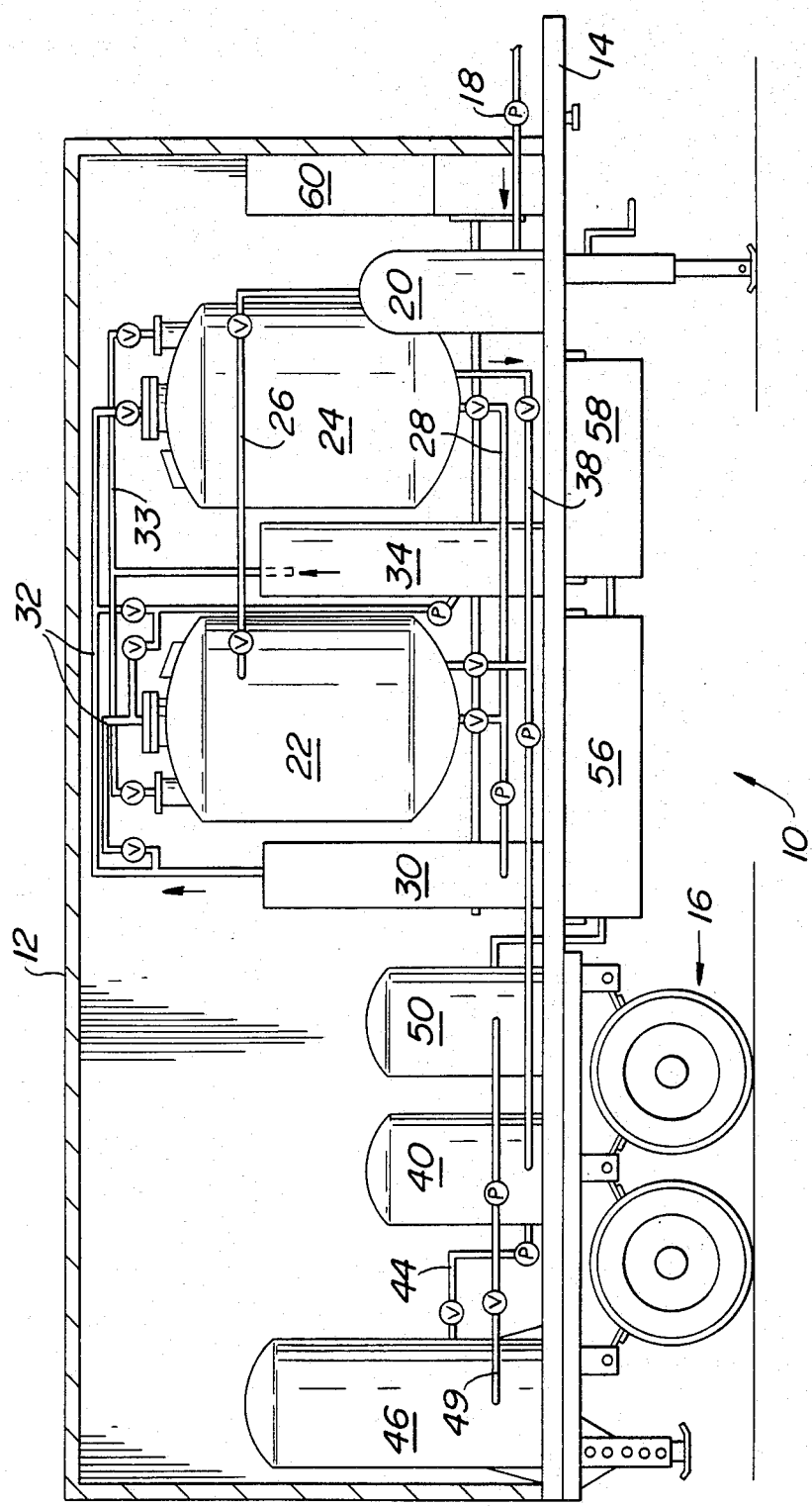
FIG. 1 is a sectional view through a trailer illustrating apparatus utilized in accordance with the present invention.
Figure 2:
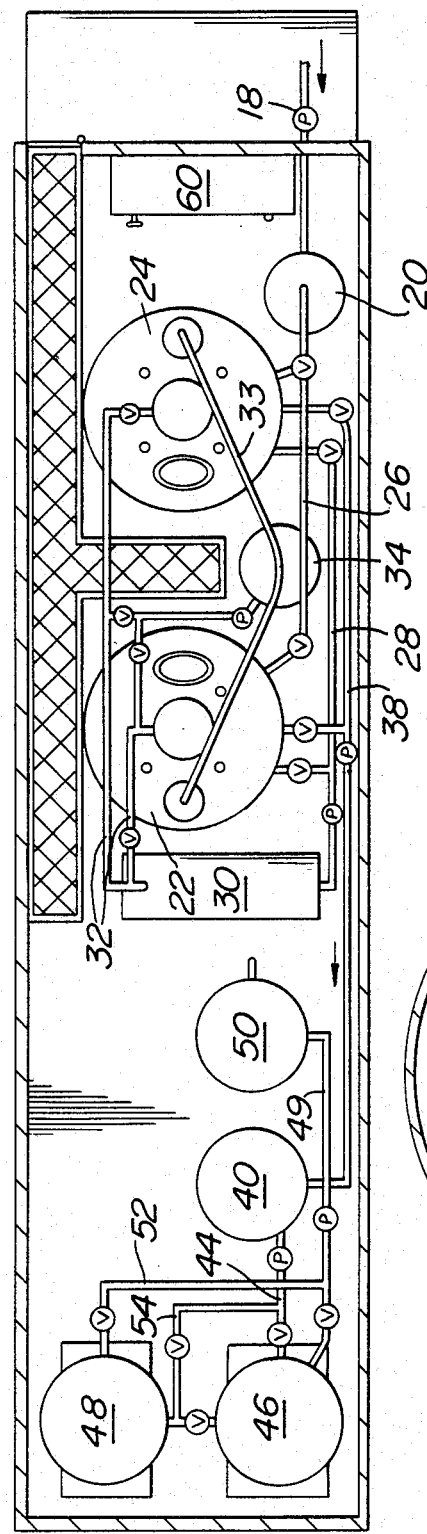
FIG. 2 is a top plan view of the apparatus shown in FIG. 1.

Referring to the drawing in detail, where like numerals indicate like elements, there is shown a vehicle designated generally as 10. Vehicle 10 is preferably a 45 foot long trailer 12 having a chassis 14 coupled to a wheel assembly 16. The trailer 12 is adapted to be pulled by a tractor in a conventional manner. The present invention enables the trailer to be driven to the site of the hydrocarbons to be treated. All of the apparatus necessary for treating hydrocarbons is disposed within the trailer 12.

A trailer 12 has an inlet pump and meter 18 adapted to be coupled to a source of hydrocarbons to be treated. Pump 18 communicates with a filter 20 designed only to remove water from the hydrocarbons. Filter 20 alternatively communicates with either reactor 22 or reactor 24 by way of valved conduit 26. Each reactor communicates at its lower end with a valved conduit 28. Conduit 28 is connected to one end a heat exchanger 30. The other end of heat exchanger 30 is connected to the top of the reactors 22, 24 by way of valved conduit 32. Conduits 28 and 32 facilitate continuous circulation of hydrocarbons through the heat exchanger 30. Each heat exchanger may also include its own heater such as a plurality of four 3 KV heaters.

A chemical injector 34 communicates at its upper end with valved conduit 33. Chemical injector 34 has an access opening not shown to facilitate introducing finely divided metallic sodium. The lower end of injector 34 communicates with each of the reactors 22, 24 by way of valved conduit 32.

Figure 3:
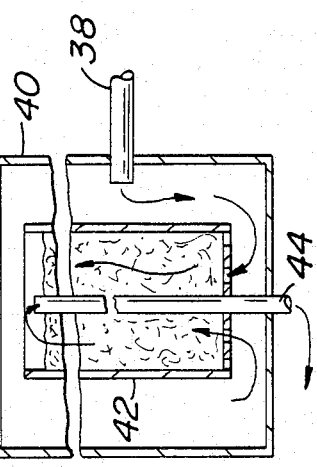
FIG. 3 is a sectional view through a separator.

The lower end of each reactor communicates with a valved conduit 38. Conduit 38 is connected to a sodium separator 40. As shown more clearly in FIG. 3, separator 40 includes a housing in which is located an upright filter 42. Filter 42 is preferably filled with steel wool. Entry into the filter 42 is from the perforated bottom. Hydrocarbons passing up through the filter 42 communicate with the upper end of a standpipe 44 and then pass downwardly through the pipe 44. The direction of flow is illustrated by arrows in FIG. 3.

The pipe 44 is coupled by way of a valve to a first clay filter 46 and then by way of conduit 49 to a final filter 50. Alternatively, discharge from clay filter 46 may be directly to clay filter 48 which communicates by way of conduit 52 with the conduit 49. Alternatively, pipe 44 may communicate directly with filter 48 by way of valve conduit 54 and thereby bypass filter 46.

The final filter 50 is preferably a ½ micron filter which polishes the hydrocarbons. Filter 50 communicates with a storage tank 56 attached to the bottom of the chassis 14. Hydrocarbons may be withdrawn from the tank 56 by way of a pump and hose disposed within the housing 58. Tank 56 preferably has a capacity of about 1,000 gallons. Pumps are provided in various conduits as shown in the drawing to maintain a uniform throughput.

The reactors 22 and 24 are utilized alternatively for batch handling of the hydrocarbons to be processed. The most common types of hydrocarbons to be processed are transformer oil containing PCB as a fire retardant. The present invention is desired to reduce PCB to less than 2 ppm. Hydrocarbons having an excess of 4,000 ppm have been successfully processed utilizing the apparatus of the present invention.

OPERATION

The vehicle 10 is transported to the location of the hydrocarbons to be processed. The source of hydrocarbons is connected to the inlet of pump 18. Pump 18 includes a meter for registering or recording the amount of hydrocarbons processed. Pump 18 pumps the hydrocarbons through filter 20 where water is removed so that the hydrocarbons are substantially free of water when introduced to one of the reactors 22, 24. Let it be assumed that the hydrocarbons are communicated from filter 20 to the reactor 22. Within the reactor 22, the hydrocarbons are heated. In addition, the hydrocarbons are pumped from the reactor 22 through the heat exchanger 30 and returned to the reactor 22.

Temperature and flow rates are monitored on a control panel 60. When the temperature has reached about 130° C., the valves associated with conduits 32 and 33 are manipulated so as to cause the circulating hydrocarbons to flow through the injector 34 and melt at a predetermined amount of finely divided metallic sodium. The preferred embodiment of the present invention involves adding 0.03 grams of sodium for each ppm of PCB for each gallon of hydrocarbon being treated. For a 500 gallon batch, 42.7 pounds of sodium are added to injector 34 where the hydrocarbons had 4,179 ppm of PCB.

Since insertion of the injector into the flow circuit reduces the temperature of the hydrocarbons by about 7° to 10° F., the mixture is directed from reactor 22 through the heat exchanger and to the injector and back to the reactor. By locating a pump in conduit 33 at the inlet of the injector, the flow of hydrocarbon can be directed solely between the reactor and the injector after the hydrocarbon is brought back to temperature. Within reactor 22, the mixture is agitated. At 15 minute intervals a sample of the hydrocarbons being processed is analyzed with a gas chromatograph to ascertain the ppm of the PCB. When the ppm of PCB is less than 2 ppm, valves associated with conduit 38 are open so that the mixture may be directed by way of conduit 38 to the separator 40.

In the sodium separator 40, the hydrocarbons pass upwardly through the steel wool filter 42 and downwardly through the standpipe 44. Sodium chloride and phenyl polymers which result from the reaction of the sodium with the PCB are retained within the separator 40. Thereafter, the decontaminated hydrocarbons are pumped through one or both of the clay filters 46, 48 to the final filter 50. From the final filter 50, the hydrocarbons are pumped to the storage tank 56. While sodium is being added to the hydrocarbons being processed in the reactor 22, a second batch may be processed by filling reactor 24 and circulating hydrocarbons containing PCB from reactor 24 and through the heat exchanger 30. Although potassium and lithium may be used, finely divided metallic sodium is preferred as the source of the metal for combining with the chlorine in PCB since it is the least volatile, the least expensive, and works the fastest.

The temperature of 130° C. was chosen since metallic sodium will liquify and flow rapidly at that temperature. While higher temperatures may be used, we prefer to avoid such higher temperatures so as to avoid producing other toxic substances such as dioxin. Since the melting point of sodium is 97.6° C., a suitable temperature range for the temperature of hydrocarbon is 110° C. to 140° C. with 130° C. being preferred since sodium flows readily and rapidly mixes with the hydrocarbon at that temperature. No attempt is made herein to describe features of common knowledge such as how to measure the amount of PCB present, closing of valves which should be closed, periodic removal of residue in collector 40, etc.

The present invention may be embodied in other specific forms without departing from the spirit or essential attribues thereof, and accordingly, reference should be made to the appended claims, rather than to the foregoing specification, as indicating the scope of the invention.

We claim:

1. Apparatus for removing PCB from hydrocarbons comprising a common support for the following components and the components themselves:

a filter for removing water from hydrocarbons, a reactor, a heat exchanger for heating hydrocarbons containing PCB, a vessel selectively communicating with said reactor for introducing sodium into the hydrocarbons for reacting with the chlorine in the PCB, and a separator for separating reactant sodium chloride and phenyl polymer from the hydrocarbon having less than two ppm PCB, the outlet of said filter being connected to said reactor, an outlet of said reactor being coupled to an inlet of said heat exchanger and an outlet of said heat exchanger being coupled to an inlet of said reactor so that hydrocarbon containing PCB may flow through a closed circuit including said reactor and said heat exchanger, an outlet of said reactor being coupled to an inlet of said vessel and an outlet of said vessel being connected to an inlet of said reactor so that hydrocarbons containing PCB may selectively flow through a closed circuit including said reactor and said vessel, an outlet of said reactor being connected to an inlet of said separator.

2. Apparatus in accordance with claim 1 wherein said common support is a mobile vehicle adapted to be transported to the site of hydrocarbons to be decontaminated.

3. Apparatus in accordance with claim 1 wherein the inlet in said first mentioned filter includes a pump and flow meter.

4. Apparatus in accordance with claim 1 wherein the separator comprises a housing, a filter member within said housing, said filter member having a perforated lower portion and containing a filter material, and a standpipe located within said filter member so that the hydrocarbons flow into said housing, through the perforations in said filter member, through said filter material and down said standpipe.

5. Apparatus in accordance with claim 4 wherein the filter material is steel wool.

6. Apparatus in accordance with claim 1 including means to selectively couple said reactor, said heat exchanger and said vessel so that hydrocarbons containing PCB may selectively flow through a closed circuit including said reactor, said heat exchanger and said vessel.

* * * * *